(12) United States Patent
Schumacher et al.

(10) Patent No.: US 11,135,405 B2
(45) Date of Patent: Oct. 5, 2021

(54) SHEATH DEVICE FOR INSERTING A CATHETER

(71) Applicant: ECP ENTWICKLUNGSGESELLSCHAFT MBH, Charlottenburg (DE)

(72) Inventors: Joerg Schumacher, Teltow (DE); Lars Bredenbreuker, Berlin (DE); Robert Decke, Berlin (DE)

(73) Assignee: ECP ENTWICKLUNGSGESELLSCHAFT MBH, Aachen (DE)

(*) Notice: Subject to any disclaimer, the term of this patent is extended or adjusted under 35 U.S.C. 154(b) by 12 days.

(21) Appl. No.: 16/696,664

(22) Filed: Nov. 26, 2019

(65) Prior Publication Data

US 2020/0164182 A1 May 28, 2020

Related U.S. Application Data

(63) Continuation of application No. 15/474,592, filed on Mar. 30, 2017, now Pat. No. 10,525,238, which is a
(Continued)

(30) Foreign Application Priority Data

Dec. 22, 2011 (EP) ........................ 1075272

(51) Int. Cl.
*A61M 25/06* (2006.01)
*A61M 39/02* (2006.01)
(Continued)

(52) U.S. Cl.
CPC ........ *A61M 25/0668* (2013.01); *A61M 25/01* (2013.01); *A61M 25/0662* (2013.01);
(Continued)

(58) Field of Classification Search
CPC .............. A61M 25/0668; A61M 25/10; A61M 25/0662; A61M 2039/0258;
(Continued)

(56) References Cited

U.S. PATENT DOCUMENTS 2,350,534 A 6/1944 Arthur
3,333,127 A 7/1967 Congdon et al.
(Continued)

FOREIGN PATENT DOCUMENTS

CA 2613175 A1 1/2007
CA 2632420 A1 6/2007
(Continued)

OTHER PUBLICATIONS

Brochure Impella Pumpsystem of Impella CardioSystems AG, "Turning Lives Around," Aug. 2003 (4 pages).
(Continued)

*Primary Examiner* — Katrina M Stransky
(74) *Attorney, Agent, or Firm* — Botos Churchill IP Law LLP

(57) ABSTRACT

In a sheath device for inserting a catheter into a patient's body, comprising a first sheath having a proximal end and a distal end, wherein when used as intended the distal end of the first sheath is provided for arrangement in the patient's body and the proximal end of the first sheath is provided for arrangement outside the patient's body, and wherein the first sheath comprises a tubular section and a sheath housing, which is disposed at the proximal end of the section and comprises a receiving channel for a catheter, according to the invention the tubular section is detachably held in a clamping element of the sheath housing in a non-positive manner so as to be able to easily shorten the tubular section.

22 Claims, 7 Drawing Sheets

Related U.S. Application Data continuation of application No. 13/261,902, filed as application No. PCT/EP2012/076587 on Dec. 21, 2012, now Pat. No. 9,642,984.

(60) Provisional application No. 61/579,198, filed on Dec. 22, 2011.

(51) Int. Cl.

| | |
|---|---|
| *A61M 39/06* | (2006.01) |
| *A61M 25/01* | (2006.01) |
| *A61M 25/00* | (2006.01) |
| *A61M 60/148* | (2021.01) |
| *A61M 60/205* | (2021.01) |
| *A61B 17/00* | (2006.01) |
| *A61M 60/135* | (2021.01) |
| *A61M 60/414* | (2021.01) |
| *A61M 60/857* | (2021.01) |

(52) U.S. Cl.
CPC ........ *A61M 39/0247* (2013.01); *A61M 39/06* (2013.01); *A61M 60/148* (2021.01); *A61M 60/205* (2021.01); *A61B 2017/00469* (2013.01); *A61M 25/0097* (2013.01); *A61M 60/135* (2021.01); *A61M 60/414* (2021.01); *A61M 60/857* (2021.01); *A61M 2025/0188* (2013.01); *A61M 2025/0675* (2013.01); *A61M 2025/0681* (2013.01); *A61M 2039/0258* (2013.01); *A61M 2039/0279* (2013.01); *A61M 2039/062* (2013.01); *A61M 2039/0626* (2013.01); *A61M 2039/0673* (2013.01)

(58) Field of Classification Search
CPC .............. A61M 39/0247; A61M 39/06; A61M 2025/0188; A61M 2039/0279; A61M 2039/062; A61M 2039/0673; A61M 60/148; A61B 2017/00469
See application file for complete search history.

(56) References Cited

U.S. PATENT DOCUMENTS

| | | |
|---|---|---|
| 3,354,833 A | 11/1967 | Laing |
| 3,489,145 A | 1/1970 | Judson et al. |
| 3,936,683 A | 2/1976 | Walker |
| 4,065,234 A | 12/1977 | Yoshiyuki et al. |
| 4,115,040 A | 9/1978 | Knorr |
| 4,135,253 A | 1/1979 | Reich et al. |
| 4,153,048 A | 5/1979 | Magrini |
| 4,420,851 A | 12/1983 | Wiener |
| 4,610,674 A | 9/1986 | Suzuki et al. |
| 4,679,558 A | 7/1987 | Kensey et al. |
| 4,686,982 A | 8/1987 | Nash |
| 4,699,611 A | 10/1987 | Bowden |
| 4,728,319 A | 3/1988 | Masch |
| 4,747,821 A | 5/1988 | Kensey et al. |
| 4,747,840 A | 5/1988 | Ladika et al. |
| 4,749,376 A | 6/1988 | Kensey et al. |
| 4,753,221 A | 6/1988 | Kensey et al. |
| 4,777,951 A | 10/1988 | Cribier et al. |
| 4,846,152 A | 7/1989 | Wampler et al. |
| 4,895,557 A | 1/1990 | Moise et al. |
| 4,919,647 A | 4/1990 | Nash |
| 4,984,972 A | 1/1991 | Clausen et al. |
| 5,011,469 A | 4/1991 | Buckberg et al. |
| 5,017,103 A | 5/1991 | Dahl |
| 5,037,403 A | 8/1991 | Garcia |
| 5,042,984 A | 8/1991 | Kensey et al. |
| 5,061,256 A | 10/1991 | Wampler |
| 5,097,849 A | 3/1992 | Kensey et al. |
| 5,139,486 A | 8/1992 | Moss |
| 5,147,186 A | 9/1992 | Buckholtz |
| 5,158,279 A | 10/1992 | Laffey et al. |
| 5,163,431 A | 11/1992 | Griep |
| 5,167,636 A | 12/1992 | Clement |
| 5,169,378 A | 12/1992 | Figuera |
| 5,234,425 A | 8/1993 | Fogarty et al. |
| 5,250,059 A | 10/1993 | Andreas et al. |
| 5,275,580 A | 1/1994 | Yamazaki |
| 5,282,790 A | 2/1994 | Clement |
| 5,304,142 A | 4/1994 | Liebl et al. |
| 5,320,611 A | 6/1994 | Bonutti et al. |
| 5,357,963 A | 10/1994 | Mayol et al. |
| 5,376,114 A | 12/1994 | Jarvik |
| 5,395,341 A | 3/1995 | Slater |
| 5,397,310 A | 3/1995 | Chu et al. |
| 5,405,383 A | 4/1995 | Barr |
| 5,407,430 A | 4/1995 | Peters |
| 5,421,338 A | 6/1995 | Crowley et al. |
| 5,480,392 A | 1/1996 | Mous |
| 5,488,960 A | 2/1996 | Toner |
| 5,492,530 A | 2/1996 | Fischell et al. |
| 5,533,986 A | 7/1996 | Mottola et al. |
| 5,536,255 A | 7/1996 | Moss |
| 5,573,517 A | 11/1996 | Bonutti et al. |
| 5,653,697 A | 8/1997 | Quiachon et al. |
| 5,749,855 A | 5/1998 | Reitan |
| 5,827,171 A | 10/1998 | Dobak et al. |
| 5,863,179 A | 1/1999 | Westphal et al. |
| 5,888,241 A | 3/1999 | Jarvik |
| 5,911,702 A | 6/1999 | Romley et al. |
| 5,935,122 A | 8/1999 | Fourkas et al. |
| 5,938,672 A | 8/1999 | Nash |
| 5,954,745 A | 9/1999 | Gertler et al. |
| 5,971,993 A | 10/1999 | Hussein et al. |
| 5,984,944 A | 11/1999 | Forber |
| 6,001,078 A | 12/1999 | Reekers |
| 6,054,788 A | 4/2000 | Dombrovski et al. |
| 6,083,260 A | 7/2000 | Aboul-Hosn |
| 6,123,725 A | 9/2000 | Aboul-Hosn |
| 6,129,704 A | 10/2000 | Forman et al. |
| 6,183,220 B1 | 2/2001 | Ohara et al. |
| 6,197,016 B1 | 3/2001 | Fourkas et al. |
| 6,245,007 B1 * | 6/2001 | Bedingham ......... A61M 60/829 600/16 |
| 6,338,730 B1 | 1/2002 | Bonutti et al. |
| 6,350,278 B1 | 2/2002 | Lenker et al. |
| 6,413,222 B1 | 7/2002 | Pantages et al. |
| 6,428,556 B1 | 8/2002 | Chin |
| 6,517,528 B1 | 2/2003 | Pantages et al. |
| 6,533,716 B1 | 3/2003 | Schmitz-Rode et al. |
| 6,537,247 B2 | 3/2003 | Shannon |
| 6,540,712 B1 | 4/2003 | Parodi et al. |
| 6,544,216 B1 | 4/2003 | Sammler et al. |
| 6,613,038 B2 | 9/2003 | Bonutti et al. |
| 6,656,153 B1 | 12/2003 | Sakai et al. |
| 6,692,462 B2 | 2/2004 | Mackenzie et al. |
| 6,814,715 B2 | 11/2004 | Bonutti et al. |
| 6,841,910 B2 | 1/2005 | Gery |
| 6,858,001 B1 | 2/2005 | Aboul-Hosn |
| 6,974,436 B1 | 12/2005 | Aboul-Hosn et al. |
| 6,976,996 B1 | 12/2005 | Aboul-Hosn |
| 6,981,942 B2 | 1/2006 | Khaw et al. |
| 7,022,100 B1 | 4/2006 | Aboul-Hosn et al. |
| 7,025,746 B2 | 4/2006 | Tal |
| 7,027,875 B2 | 4/2006 | Siess et al. |
| 7,166,088 B2 | 1/2007 | Heuser |
| 7,186,222 B1 * | 3/2007 | Callister ............ A61B 5/0008 600/549 |
| 7,393,181 B2 | 7/2008 | McBride et al. |
| 7,632,254 B1 * | 12/2009 | Bjorkman ......... A61M 25/0668 251/369 |
| 7,646,376 B2 | 1/2010 | Blersch |
| 7,722,567 B2 | 5/2010 | Tal |
| 7,731,675 B2 | 6/2010 | Aboul-Hosn et al. |
| 7,841,976 B2 | 11/2010 | McBride et al. |
| 7,914,492 B2 | 3/2011 | Heuser |
| 7,927,068 B2 | 4/2011 | McBride et al. |
| 8,066,674 B2 | 11/2011 | Heuser |
| 8,079,948 B2 | 12/2011 | Shifflette |
| 8,439,859 B2 | 5/2013 | Pfeffer et al. |

(56) References Cited

U.S. PATENT DOCUMENTS

| | | |
|---|---|---|
| 8,597,277 B2 | 12/2013 | Lenker et al. |
| 8,672,888 B2 | 3/2014 | Tal |
| 8,758,402 B2 | 6/2014 | Jenson et al. |
| 8,888,728 B2 | 11/2014 | Aboul-Hosn et al. |
| 9,623,228 B2 | 4/2017 | Ryan et al. |
| 10,525,238 B2 * | 1/2020 | Schumacher .......... A61M 25/01 |
| 2001/0000528 A1 | 4/2001 | Cho |
| 2002/0120226 A1 | 8/2002 | Beck |
| 2002/0151799 A1 | 10/2002 | Pantages et al. |
| 2003/0135940 A1 | 7/2003 | Lev et al. |
| 2003/0208097 A1 | 11/2003 | Aboul-Hosn et al. |
| 2004/0022640 A1 | 2/2004 | Siess et al. |
| 2004/0044266 A1 | 3/2004 | Siess et al. |
| 2004/0113502 A1 | 6/2004 | Li et al. |
| 2004/0147877 A1 | 7/2004 | Heuser |
| 2004/0193046 A1 | 9/2004 | Nash et al. |
| 2004/0230287 A1 | 11/2004 | Hartley et al. |
| 2004/0260237 A1 | 12/2004 | Squadrito |
| 2005/0135942 A1 | 6/2005 | Wood et al. |
| 2005/0149097 A1 | 7/2005 | Regnell et al. |
| 2005/0149105 A1 | 7/2005 | Leeflang et al. |
| 2005/0245892 A1 | 11/2005 | Elkins et al. |
| 2006/0008349 A1 | 1/2006 | Khaw |
| 2006/0062672 A1 | 3/2006 | McBride et al. |
| 2006/0135981 A1 | 6/2006 | Lenker et al. |
| 2006/0195004 A1 | 8/2006 | Jarvik |
| 2006/0287574 A1 | 12/2006 | Chin |
| 2007/0118072 A1 | 5/2007 | Nash |
| 2007/0299499 A1 | 12/2007 | Hartley et al. |
| 2008/0004569 A1 | 1/2008 | McCrystle et al. |
| 2008/0004571 A1 | 1/2008 | Voss |
| 2008/0033396 A1 | 2/2008 | Danek et al. |
| 2008/0046005 A1 | 2/2008 | Lenker et al. |
| 2008/0051734 A1 | 2/2008 | Bonutti et al. |
| 2008/0051821 A1 | 2/2008 | Gephart |
| 2008/0065011 A1 | 3/2008 | Marchand et al. |
| 2008/0082165 A1 | 4/2008 | Wilson et al. |
| 2008/0097386 A1 | 4/2008 | Osypka |
| 2008/0103591 A1 | 5/2008 | Siess |
| 2008/0114339 A1 | 5/2008 | McBride et al. |
| 2008/0132747 A1 | 6/2008 | Shifflette |
| 2008/0177249 A1 | 7/2008 | Heuser et al. |
| 2008/0183136 A1 | 7/2008 | Lenker et al. |
| 2008/0319387 A1 * | 12/2008 | Amisar .............. A61M 25/0111 604/95.04 |
| 2009/0012476 A1 | 1/2009 | Catlin |
| 2009/0024201 A1 * | 1/2009 | Fitzgerald ................. A61F 2/95 623/1.12 |
| 2009/0060743 A1 | 3/2009 | McBride et al. |
| 2009/0062597 A1 | 3/2009 | Shifflette |
| 2009/0088609 A1 | 4/2009 | Schmitz-Rode et al. |
| 2009/0093764 A1 | 4/2009 | Pfeffer et al. |
| 2009/0093796 A1 | 4/2009 | Pfeffer et al. |
| 2009/0218728 A1 | 9/2009 | Moyer |
| 2009/0227892 A1 | 9/2009 | Krombach et al. |
| 2009/0240202 A1 | 9/2009 | Drasler et al. |
| 2009/0318867 A1 * | 12/2009 | Amisar ................. A61M 25/06 604/164.05 |
| 2010/0004730 A1 | 1/2010 | Benjamin et al. |
| 2010/0030161 A1 * | 2/2010 | Duffy ................ A61M 25/0668 604/246 |
| 2010/0160863 A1 | 6/2010 | Heuser |
| 2010/0210895 A1 | 8/2010 | Aboul-Hosn et al. |
| 2010/0268017 A1 | 10/2010 | Siess |
| 2011/0071338 A1 | 3/2011 | McBride et al. |
| 2013/0035628 A1 | 2/2013 | Garrison et al. |
| 2013/0041202 A1 | 2/2013 | Toellner |
| 2013/0066140 A1 | 3/2013 | McBride et al. |
| 2013/0131718 A1 | 5/2013 | Jenson et al. |
| 2013/0197621 A1 | 8/2013 | Ryan et al. |
| 2013/0317438 A1 | 11/2013 | Ellingwood et al. |
| 2013/0317481 A1 | 11/2013 | Ellingwood et al. |
| 2014/0018732 A1 | 1/2014 | Bagaoisan et al. |
| 2015/0073202 A1 | 3/2015 | Aboul-Hosn et al. |
| 2016/0066948 A1 | 3/2016 | Ellingwood et al. |
| 2016/0220358 A1 | 8/2016 | Wilson et al. |
| 2016/0354583 A1 | 12/2016 | Ellingwood et al. |
| 2017/0056063 A1 | 3/2017 | Ellingwood et al. |
| 2017/0281908 A1 | 10/2017 | Ellingwood et al. |

FOREIGN PATENT DOCUMENTS

| | | |
|---|---|---|
| CA | 2701810 A1 | 4/2009 |
| DE | 4414903 A1 | 11/1995 |
| DE | 29804046 U1 | 4/1998 |
| DE | 10059714 C1 | 5/2002 |
| DE | 102005039950 A1 | 3/2007 |
| EP | 0364293 A2 | 4/1990 |
| EP | 0445782 A1 | 9/1991 |
| EP | 0768900 A1 | 4/1997 |
| EP | 914171 A2 | 5/1999 |
| EP | 0916359 A1 | 5/1999 |
| EP | 1034808 A1 | 9/2000 |
| EP | 1207934 A2 | 5/2002 |
| EP | 2047872 B1 | 9/2010 |
| EP | 2229965 A1 | 9/2010 |
| EP | 2347778 A1 | 7/2011 |
| EP | 2399639 A1 | 12/2011 |
| FR | 2788223 A1 | 7/2000 |
| JP | H04126158 A | 4/1992 |
| WO | 9944651 A1 | 9/1999 |
| WO | 9958170 A1 | 11/1999 |
| WO | 2000019097 A1 | 4/2000 |
| WO | 2000043053 A1 | 7/2000 |
| WO | 2001083016 A2 | 11/2001 |
| WO | 2002022200 A1 | 3/2002 |
| WO | 0243791 A1 | 6/2002 |
| WO | 2003103745 A2 | 12/2003 |
| WO | 2006020942 A1 | 2/2006 |
| WO | 2006034158 A2 | 3/2006 |
| WO | 2010063494 A1 | 6/2010 |
| WO | 2011089022 A1 | 7/2011 |
| WO | 2011115048 A1 | 9/2011 |

OTHER PUBLICATIONS

Buecker A et al., "Use of a Nonmetallic Guide Wire for Magnetic Resonance-Guided Coronary Artery Catheterization," Investigative Radiology, 39:11, pp. 656-660 (2004).

Compendium of Technical and Scientific Information for the Hemopump Temporary Cardiac Assist System, 1988 (15 pages).

Dekker, Andre, et al, "Efficacy of a New Intraaortic Propeller Pump vs the Intraaortic Balloon Pump," Chest Journal; Jun. 2003 (7 pages).

Frazier, O.H., et al, "First Human Use of the Hemopump, A Cather-Mounted Ventricular Assist Device," Ann Thorac Surg., Feb; 49(2): pp. 299-304 (1990).

International Preliminary Report on Patentability, from PCT/EP08/008858, dated Jun. 7, 2011.

JOMED Reitan Catheter Pump Brochure, www.iomed.com/rcp (undated) (6 paqes).

Lueger, Lexikon der Technik, "Lexikon der Feinwerktechnik", vol. 13, Deutsche Verlags-Anstalt GmbH, Stuttgart, seite 551 (1968).

Reitan, Oyvind et al, "Hydrodynamic Properties of a New Percutaneous Intra-aortic Axial Flow Pump," ASAIO Journal; May-June; vol. 16; paoes 323-329 (2000).

Rothman, Martin T, "The Reitan Catheter Pump: A New Versatile Approach for Hemodynamic Support," London Chest Hospital Barts & The Long NHS Trust, presented at TCT Conference, Oct. 24-26, 2006, (40 pages).

Schmitz-Rode, T et al, "Temporary Pulmonary Stent Placement as Emergency Treatment of Pulmonary Embolism," Journal of the American College of Cardiology, 48:4, pp. 812-816 (2006).

Schmitz-Rode, T et al., "An Expandable Percutaneous Catheter Pump for Left Ventricular Support," Journal of the American College of Cardiology, 45:11, pp. 1856-1861 (2005).

Siess, Thorsten, "Systemanalyse and Entwicklung intravasaler Rotationspumpen zur Herzunterstutzung," Helmholtz-Institut, Jun. 24, 1998 (105 pages) and partial English translation (37 pages).

(56) References Cited

OTHER PUBLICATIONS

Verma, R et al., "Evaluation of a Newly Developed Percutaneous Thrombectomy Basket Device in Sheep with Central Pulmonary Embolisms," Investigative Radiology, 41:10, pp. 729-734 (2006).
Wampler, Richard, K., "In Vivo Evaluation of a Peripheral Vascular Access Axial Flow Blood Pump," ASAIO Trans., Jul-Sep;34(3): pp. 450-454 (1988).

* cited by examiner

SHEATH DEVICE FOR INSERTING A CATHETER

CROSS-REFERENCE TO RELATED APPLICATIONS

This application is a continuation of U.S. application Ser. No. 15/474,592, filed Mar. 30, 2017 (now allowed), which is a continuation of U.S. application Ser. No. 13/261,902, filed May 21, 2014, which is a national stage entry of PCT/EP2012/076587, filed Dec. 21, 2012, which claims the benefit of U.S. Provisional Patent Application No. 61/579,198, filed Dec. 22, 2011, and European Patent Application No. 11075272.2, filed Dec. 22, 2011. The disclosures of each of the foregoing applications are incorporated herein by reference in their entirety.

TECHNICAL FIELD

The invention resides in the mechanical field and can advantageously be used in medical engineering. It relates to a sheath device for inserting a catheter into a patient's body, wherein the sheath leads into the patient's body and a proximal end of the sheath protrudes therefrom. The sheath provides a lumen, through which a catheter can be inserted into the patient's body.

BACKGROUND OF THE INVENTION

Such sheath devices are known in principle. They are used to insert various catheters, for example in the minimally invasive medical field. Such a sheath can, for example, be provided for inserting a blood pump for cardiac support, such a unit comprising a distal pump unit, a hollow catheter and a drive shaft which is guided through the hollow catheter. In miniaturized form, such pumps are often times designed so that they can be radially compressed and inserted, in the compressed state, together with the catheter through a blood vessel of the body. The pump can then be expanded at the site of use, for example in a blood vessel or in a ventricle. In the expanded state, with delivery elements activated, such a pump can then attain the required pumping capacity.

In addition to such compressible heart pumps, other functional elements are also conceivable, which are introduced into a cavity of a body by means of a sheath according to the invention, such as stents or milling heads for removing plaque from vessels.

Compared to a direct insertion, inserting such functional elements and catheters by means of a sheath is considerably easier and also associated with fewer medical risks.

The sheath itself can be inserted, for example into a vascular system, using the known Seldinger Technique. For this purpose, first an opening is introduced in a body vessel by means of a puncturing needle, whereupon a guide wire is pushed in. A dilator is then optionally introduced via the guide wire, and thereupon the sheath itself is pushed in. The guide wire can then be removed, unless it is required for further guide tasks, and other elements can be introduced via the sheath.

A corresponding method is known from WO 02/43791, for example. According to this document, a heart pump is advanced along a guide wire into the left ventricle of a patient and a pump unit is advanced out of the sheath through the vascular system to the ventricle.

A corresponding fluid pump, which is provided for high rotational speeds so as to achieve a corresponding pumping capacity, in the form of a blood pump is likewise known from WO 02/43791 A1, but also from EP 2047872. EP 2047872A1 describes a pump which comprises a distal pump unit, to which a proximal shaft hollow catheter adjoins. A drive shaft extending in the shaft catheter is connected to a drive unit for driving the rotor of the pump.

Using a convenient sheath for inserting a catheter, notably comprising a drive shaft, has the advantage that the catheter, and more particularly a drive shaft, experiences less mechanical stress during insertion. This is advantageous in particular with high mechanical stresses to which a drive shaft is exposed when a blood pump is operated.

For a convenient use of a corresponding sheath for inserting a catheter, notably comprising a distal pump unit, it is desirable to be able to advance the sheath, together with the hollow catheter, as close as possible to the vicinity of the site of use and then remove the shaft catheter or the pump from the sheath, so as to then be able to retract the sheath at least a certain distance. The unit to be introduced is thus moved the shortest possible distance in the vascular system or corresponding cavities of the patient's body outside a sheath, so that the strain on the vascular walls due to insertion of the foreign object as well as the mechanical stress of the unit to be inserted are substantially reduced.

On the other hand, such a procedure requires a corresponding excess length of the sheath, which after being advanced and subsequently retracted typically protrudes a certain distance from the patient's body.

BRIEF SUMMARY OF THE INVENTION

It is the object of the present invention to advantageously design a corresponding sheath device so that it is particularly easy to handle.

According to the invention, a sheath device for inserting a catheter into a patient's body comprises a first sheath having a proximal end and a distal end, wherein the distal end of the first sheath is disposed inside the patient's body when the sheath is used as intended, while the proximal end protrudes from the patient's body. The first sheath additionally has a tubular section and a sheath housing, which is disposed at the proximal end of the section and comprises a receiving channel for a strand-shaped body, and more particularly for a catheter.

Because the tubular section is detachably held in a clamping element of the sheath housing in a non-positive manner, the sheath device can first be pushed into the patient's body by a certain distance so as to insert the catheter into the patient's body, the catheter can then be extracted and the sheath device can be pulled a certain distance out of the patient's body. The tubular section can then be released from the clamping particularly easily, and it can be shortened and re-clamped.

This makes it particularly easy to cut the sheath device to the suitable size after use, so that it does not protrude from the patient's body any further than necessary.

According to an advantageous embodiment of the invention, the tubular section can be displaced into the sheath housing when the clamping element is released. The tubular section can thus be accommodated in the sheath housing, removed within the sheath housing or removed through a proximal opening of the sheath housing.

It seems to be particularly useful for the tubular section to lead into the sheath housing in direct extension of the receiving channel for the catheter. This design makes the insertion of a catheter into the tubular section particularly simple, in that the catheter is first inserted into the sheath housing, guided in the receiving channel thereof and thus directed without effort to the mouth of the tubular section. It can thus be assured that the insertion of the catheter into the proximal end of the sheath device is simplified and can be reliably carried out.

This design also allows the proximal end of the tubular section of the sheath to be easily pushed into the receiving channel inside the sheath housing, so as to either be accommodated there or be removed.

According to a further advantageous embodiment of the invention, the clamping element comprises an elastically deformable clamping ring, which surrounds the tubular section and can be pressed by a manipulating element such that the ring radially clamps the tubular section, such a clamping element has a particularly simple mechanical design, is reliable, saves space and is easy to operate. It effects a non-positive fixation of the tubular section, which can also easily be released again.

To this end, the clamping ring may be radially deformable by axial pressure action. The ring can be designed as an elastomeric ring for this purpose, or as a slotted ring which is made of a plastic material or a metal.

As an elastomeric ring, the clamping ring can be pressed flat, for example by means of a pressure piece, wherein the ring expands radially inward and outward, whereby the inside diameter of the ring is decreased. If the clamping ring is a slotted plastic or metal ring, it can be compressed radially inward, for example under the action of a wedge-shaped body on the radial outside of the ring. For this purpose, for example a ring having a wedge-shaped cross-section can be used, which is moved axially relative to the tubular element. The clamping ring can also have a conical cross-section. In a preferred embodiment, it is a clamping ring which also assures a fluid-tight connection between the sheath housing and the tubular element, as can be implemented in form of the aforementioned elastomeric ring, for example. However, the sealing action can also be implemented by an additional sealing element 73, for example when using a slotted plastic or metal ring.

The clamping element may comprise a screw element, for example for axially pressing a clamping ring. The screw element can then be used, for example, to press a pressure piece against the clamping ring in the axial direction.

So as to facilitate the severability of portions of the tubular section so as to shorten the same, the tubular section can advantageously have at least one predetermined breaking point at least at the proximal end, the predetermined breaking point being used to sever a longitudinal section of the tubular section. In some regions, the tubular section can comprise peripheral indents or perforations or other weakened regions of the material in the circumferential direction, for example, which can optionally also be predetermined by a molecular structure.

The tubular section can likewise have one or more predetermined breaking points or tear lines extending the axial direction, which are known in so-called peel-away introducer sheaths. In the case of such tear lines, a sheath can be opened starting at one end by pulling two or more casing parts apart and can be pulled off. For this purpose, a tubular section can also comprise handling elements at the proximal end, such as loops or tabs.

According to the invention, the sheath device can also comprise a cutting element, by means of which a part of the tubular section can be severed, or perforated, notched or scored for the purpose of easier severing. For example, one or more blades can be inserted in the sheath housing so that the tubular section is automatically notched when it is pushed through the sheath housing. Such notching can, for example, take place in the longitudinal direction of the tubular section. It is also possible to provide a blade which, during a rotation of the sheath housing relative to the tubular section, creates a cut or a weakened region of the tubular section in the circumferential direction.

Such blades can be produced from very hard material, such as a ceramic material, for example, so that even tubular sections which are reinforced, notably reinforced by a metal woven fabric, can be cut. It is also possible to provide substantially needle-shaped blades, which can cut both during a movement of the tubular section in the axial direction and during a rotation in the circumferential direction.

According to a particularly advantageous embodiment of the invention, the cutting element comprises at least one blade, which is movably guided, notably in the sheath housing, and is notably movably guided radially toward the catheter. Such a blade may be actuated by means of a handle 70 which is located on the outside of the sheath housing, so that a cut for severing a portion of the tubular section can be made using a simple manual movement when pushing the tubular section out of the patient's body and displacing it relative to the sheath housing.

In addition to a sheath device of the type described above, the invention also relates to a catheter system comprising a catheter and such a sheath device, wherein according to the invention the sheath housing advantageously may comprise a further clamping element on the proximal side of the clamping element, wherein the further clamping element is provided so as to radially clamp the catheter or so as to radially clamp a second sheath surrounding the catheter and/or a functional element which is connected to the catheter.

The corresponding further clamping element can, in principle, likewise comprise a clamping ring and can, for example, have the same design as the first clamping element so as to fix the tubular section. However, the further clamping element can also have a different design than the first clamping element and in general be designed in accordance with one of the afore-described variants of a clamping element.

The invention further relates to a method for inserting a catheter comprising a functional element disposed at the end thereof into a patient's body, wherein the catheter is inserted into the sheath housing and the tubular section and thereupon is inserted in the tubular section into the patient's, the tubular section is then pulled a certain distance out of the patient's body in the proximal direction, and the clamping elements is released and the tubular section is moved into the sheath housing.

After being moved into the sheath housing and/or pushed through the sheath housing, the tubular section can be shortened. Before or after shortening, the tubular section can again be clamped by means of the clamping element.

The shortening is advantageously carried out by tearing open the tubular section in the longitudinal direction, notably starting from the proximal end of the tubular section, and by then tearing it off.

BRIEF DESCRIPTION OF DRAWINGS

The invention will be shown in drawings and described hereafter based on an exemplary embodiment.

DETAILED DESCRIPTION OF THE INVENTION

Figure 1:
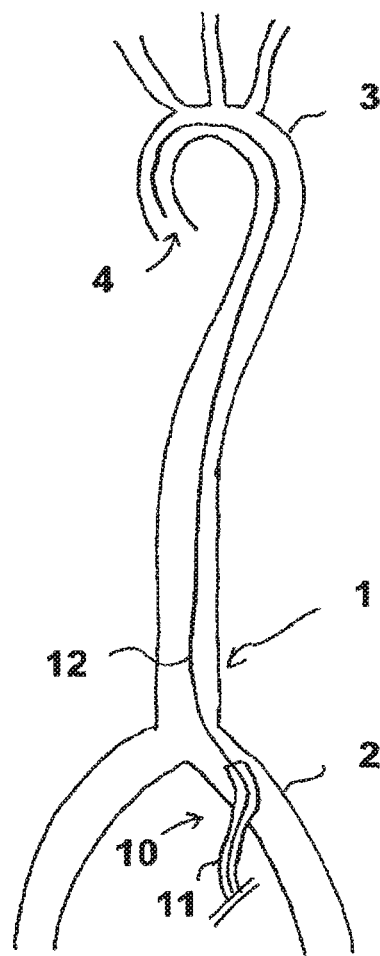
FIG. 1 is a schematic overview of a vascular system comprising an inserted first sheath.

FIG. 1 shows a schematic human vascular system 1. One of the femoral arteries 2 is located in the groin region and is connected to the aortic arch 3 via an aorta and then leads into the ventricle 4. An introducer sheath 10 is first inserted into the femoral artery 2, for example using the Seldinger Technique. The femoral artery, or any blood vessel, is punctured for this purpose, for example using a steel cannula having a cutting tip. A guide wire 12 is pushed through the steel cannula, which is inserted into the puncture site, and inserted into the left ventricle 4 retrogradely via the aortic arch 3. After the puncturing cannula is removed, the first sheath 10, which is designed as an introducer sheath and comprises a tubular section 11 and optionally a dilator, which is not shown here, is threaded on the guide wire and inserted into the vascular system through the punctured site, wherein the sheath is inserted a short distance into the lumen of the vascular system or even to the site of use of an element to be inserted. Thereafter, a fluid pump is inserted into the vascular system through the introducer sheath 10.

The tubular section 11 of the first sheath 10 is inserted into the artery such that the proximal end of the first sheath 10 is located outside the femoral artery and can thus be used for inserting a pump, for example. It is thus possible to thread the pump on the guide wire 12 so as to guide the pump into the left ventricle by means of the guide wire.

It is also possible to guide the tubular section 11 of the first sheath 10 through the guide wire into the left ventricle and to then remove the guide wire 12 from the first sheath. A pump unit that may be present is then guided through the first sheath volume into the vicinity of or into the left ventricle 4.

In the present example, the method is only illustrated based on the insertion of a pump into the left ventricle so as support a cardiac function. However, it is easy to see for a person skilled in the art that the pump, or another functional element, can also be disposed and introduced in other regions of the endogenous vascular system.

Figure 2:
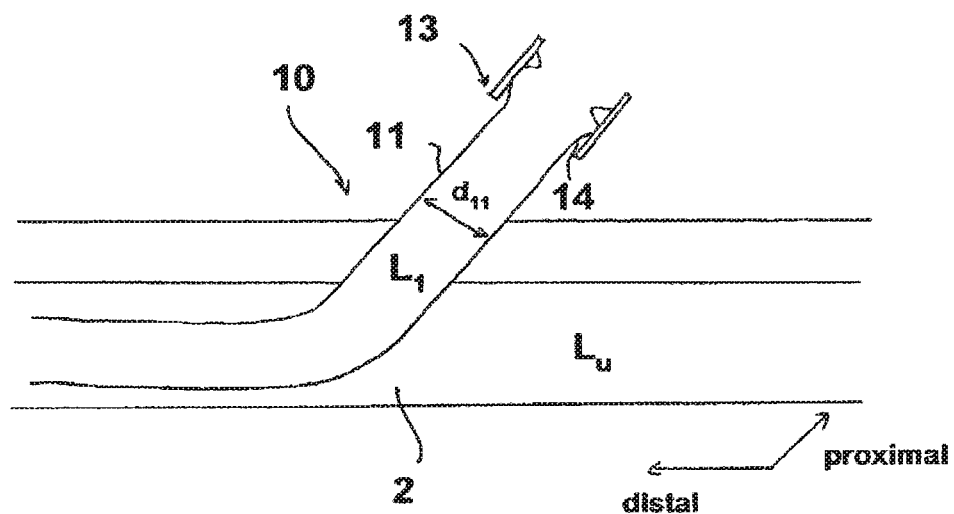
FIG. 2 is a detailed view of a section of FIG. 1.

FIG. 2 shows the region of FIG. 1 in which the first sheath 10 is guided from outside through the endogenous tissue into the lumen LG of the femoral artery 2. The first sheath comprises a tubular section 11, which is connected to a sheath housing 13 at the proximal end. The tubular section 11 defines a lumen L1, which has an inside diameter d11. This inside diameter widens toward the proximal end of the tubular section 11 in a trumpet-like shape in the region 14.

The sheath housing 13 contains a haemostatic valve, which is known from the prior art. This valve prevents fluid present in the lumen LG from exiting to the outside through the lumen L1.

Figure 3:
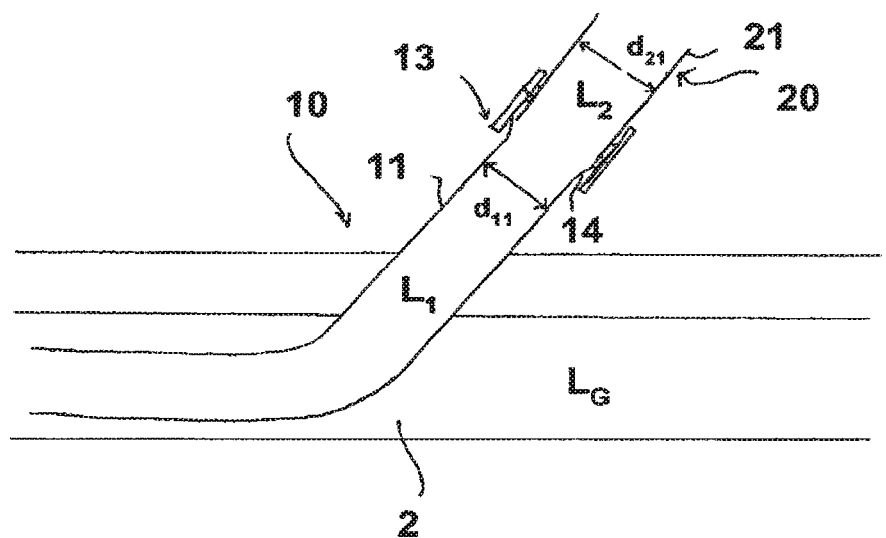
FIG. 3 shows an embodiment of the invention comprising a first sheath and a second sheath.

In the illustration of FIG. 3, the first sheath 10 of FIG. 2 is coupled to a second sheath 20. Only a tubular section 21, which defines a lumen L2 having an inside diameter d21, is shown of the second sheath 20. The outside diameter of the distal end of the second sheath 20 is such that it can be inserted into the sheath housing 13. However, the inside diameter d21 is larger than the inside diameter d11.

A pump, which is not shown and present in the lumen L2, can now be transferred into the first sheath lumen L1 from the second sheath lumen L2 by pressing. The pump is then transported through the first sheath lumen L1 to the site in the vascular system where the pump is intended to effect the action thereof. The pump can either be guided on a guide wire for this purpose, or it can be introduced without guide wire through the first sheath lumen. The first sheath can be advanced distally to the site of use of the pump before the pump is pushed out, so as to protect the pump and the vascular walls as well as the shaft catheter.

A possible embodiment of a pump 30 will be described in more detail based on FIG. 4. The pump 30 comprises a distal pump unit 31 and a shaft catheter 32, which adjoins the proximal end of the distal pump unit 31. At the proximal end, which is not shown, the shaft catheter 32 comprises a coupling for coupling the shaft catheter 32 to a drive element. The drive element can be disposed outside the patient's body and causes a flexible shaft extending in the shaft catheter 32 to rotate, which in turn drives the distal pump unit 31.

The distal pump unit comprises a pump housing 33, which is produced from intersecting nitinol struts. Portions of the nitinol housing are provided with a coating 34, which extends distally and proximally of a rotor 35 disposed in the housing 33. The rotor is connected to the shaft 36 extending through the shaft catheter 32 and thus caused to rotate. The housing and the rotor can be compressed, which is to say the pump is a self-decompressible pump. The pump deploys after the distal pump unit is pushed out at the distal end of a sheath. So as to compress the pump in preparation for the implantation, the distal pump unit is pulled into the distal end of a sheath lumen of a second sheath. The inside diameter of the sheath lumen is at least greater than the outside diameter of the shaft catheter.

The rotor may be displaceable relative to the pump housing in the axial direction, notably by means of an axial displacement of the drive shaft. However, the rotor may also be fixed in the axial direction relative to the pump housing.

The pump optionally comprises an outflow hose 37, which defines a flow duct for the pumped fluid located proximally of the rotor 35. Discharge openings, which are not shown in detail, are located at the proximal end of the outflow hose 37.

The pump can, of course, also be switched from pumping operation to suction operation, so that the pump no longer conducts fluid from the distal end to the proximal end, but vice versa.

A detailed description of a further suitable pump can be found in document EP 2 047 872 A1, for example.

The function of the system shall now be described based on FIGS. 5 to 9.

Figure 4:
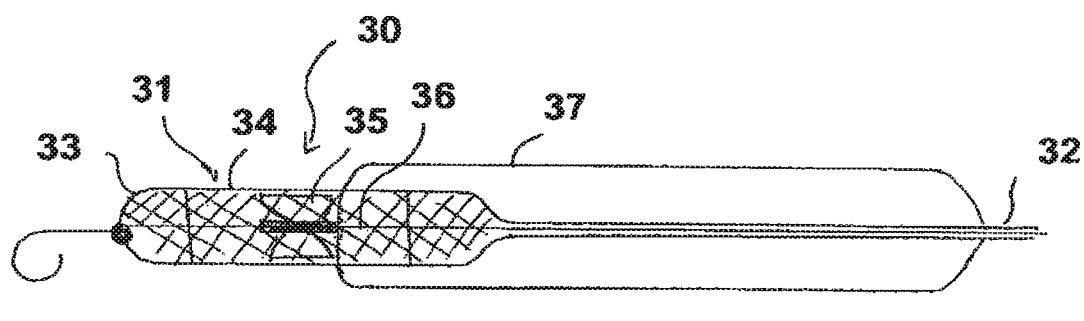
FIG. 4 shows an embodiment of a pump.
Figure 5:
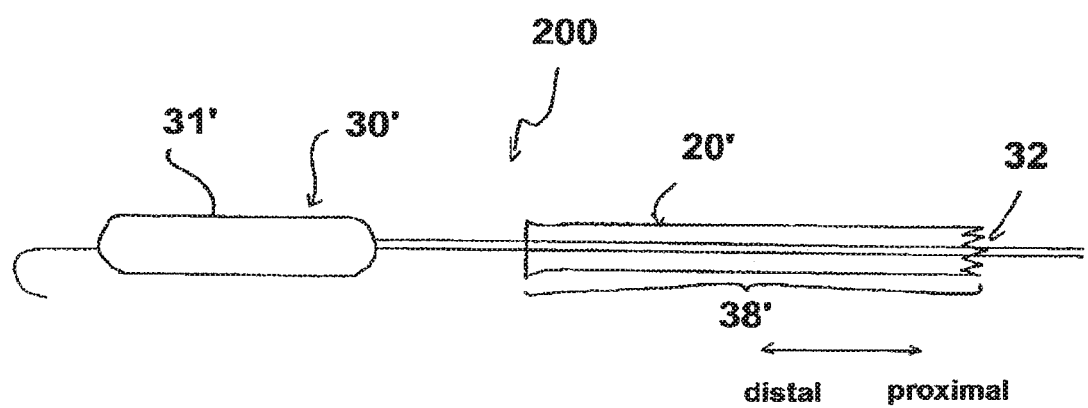
FIG. 5 shows a second sheath comprising a pump extracted therefrom.

FIG. 5 shows a pump 30', which substantially corresponds to the pump 30 of FIG. 4. To simplify matters, details of the pump are not shown. Only the bellied housing and the "pigtail" located distal of the bellied housing are shown, the pigtail preventing the heart pump from being suctioned against the cardiac wall. The shaft catheter 32' runs proximal of the distal pump unit 31'. A second sheath 20' is provided, which encloses a region 38' of the shaft catheter 32' and comprises a lumen L2, the inside diameter d21 of which is smaller than the diameter of the distal pump unit 31' when it is deployed.

The pump 30' shown in FIG. 5 is a compressible pump, which is to say the distal pump unit 31', which comprises the pump housing and the rotor located therein, among other things, is designed such that it can be compressed, which is to say that the diameter thereof can be decreased. After a quality inspector or a physician, for example, has confirmed the correct function of the pump 30', such as by observing the rotational movement of the rotor unit located in the distal pump unit 31' during a test run, the distal pump unit 31' is pulled into the lumen L2 of the second sheath 20' by pulling the shaft catheter 32' in the proximal direction. By pulling the pump into the second sheath 20', bending or damage of the shaft catheter or of the shaft extending therein is prevented. The pump 30' shown in FIG. 5 and the second sheath 20' enclosing the region 38' of the shaft catheter 32' form a system 200 which allows the function of the pump 30' to be tested in due time before surgery and the pump to be compressed by pulling the distal pump unit 31' into the distal end of the second sheath 20', and thus prevent damage to the shaft.

Although the system can be implemented both with actively decompressible pumps and with self-decompressible pumps, it is particularly suitable for self-decompressible pumps, which is to say pumps in which the distal pump unit automatically restores the original size outside the sheath.

Figure 6:
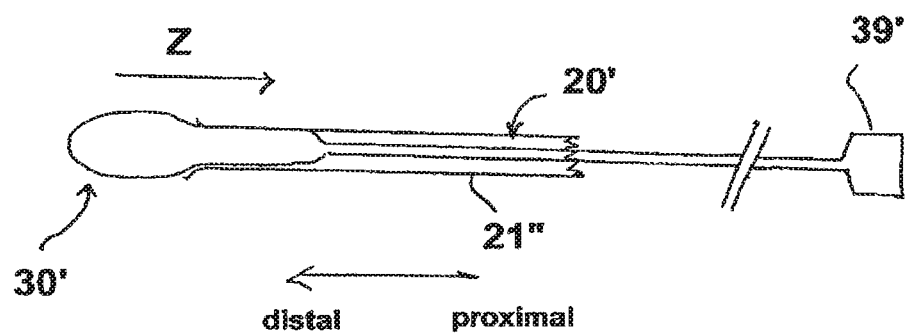
FIGS. 6, 7 show the pulling of a pump into a second sheath.

FIG. 6 shows an intermediate step when pulling the distal pump unit 30' into the lumen of the second sheath 20'. It is apparent that the distal pump unit 30' can be compressed and reduced to a smaller diameter, so that the distal pump unit 30' can be accommodated in the lumen of the second sheath 20'.

FIG. 6 further shows a coupling 39' adjoining the shaft catheter 32', the coupling allowing the shaft extending in the shaft catheter to be coupled to a drive unit. Because the coupling 39' often times has a larger outside diameter than the inside diameter of the lumen L2, the second sheath 20' is usually added from the proximal end of the shaft catheter 32' in the distal direction before the coupling 39' is mounted, so that the pump is shipped as a system 200, which is to say the pump comprising the second sheath 20' located proximal of the distal pump unit 31' and the sub-assembled coupling 39'. FIG. 6 also shows a slightly trumpet-shaped expansion of the distal end of the second sheath 20'. The trumpet-shaped expansion 24' makes it easier for the distal pump unit 31' to be pulled into the lumen L2 of the second sheath 20'.

Figure 7:
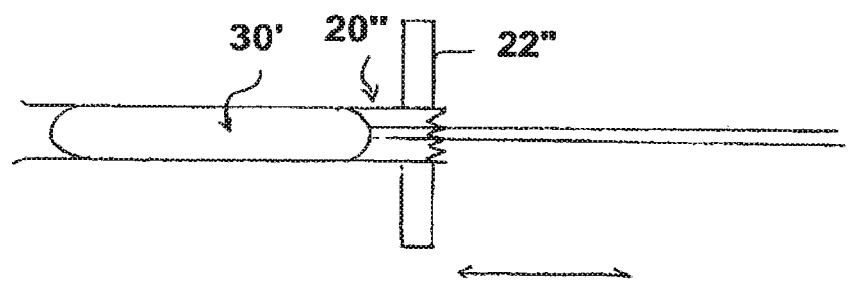

In FIG. 7 finally the distal pump unit 31' is located entirely in the lumen L2 of the second sheath 20". The second sheath 20" comprises two sub-assembled grip units 22", which allow better holding or removal of the second sheath 20" when pulling the distal pump unit 31' into the lumen L2, or subsequent tearing. If a "pigtail" is present, the same is advantageously likewise pulled into the lumen L2, so that the distal pump unit 31', together with the components of the pump located distal of the distal pump unit 31', are present in the lumen L2.

Figure 8:
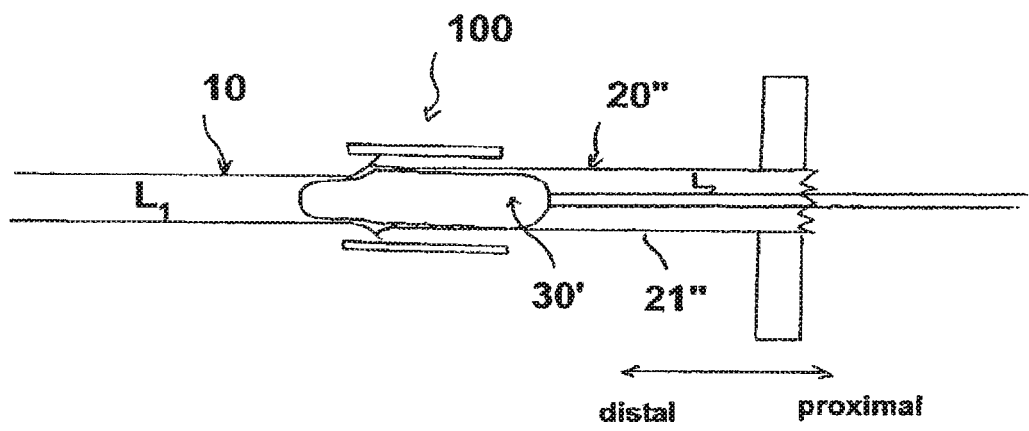
FIGS. 8, 9 show the transfer of a pump from a second sheath into a first sheath.

It is apparent from FIG. 8 how the system 200 comprising the pump 30' and second sheath 20" is combined in an operative connection with the first sheath 10 to form a system 100. First, the distal end of the second sheath 20" is inserted into the sheath housing of the first sheath 10. As soon as the distal tip of the second sheath 20" is seated against the mouth of the tubular section of the first sheath 10, the pump is transferred from the second sheath 20' into the first sheath 10' by pushing the pump in the distal direction, the pushing taking place by pushing of the shaft catheter 32'. The diameter of the distal pump unit 31' is thus reduced further to the inside diameter d11 of the lumen L1.

Figure 9:
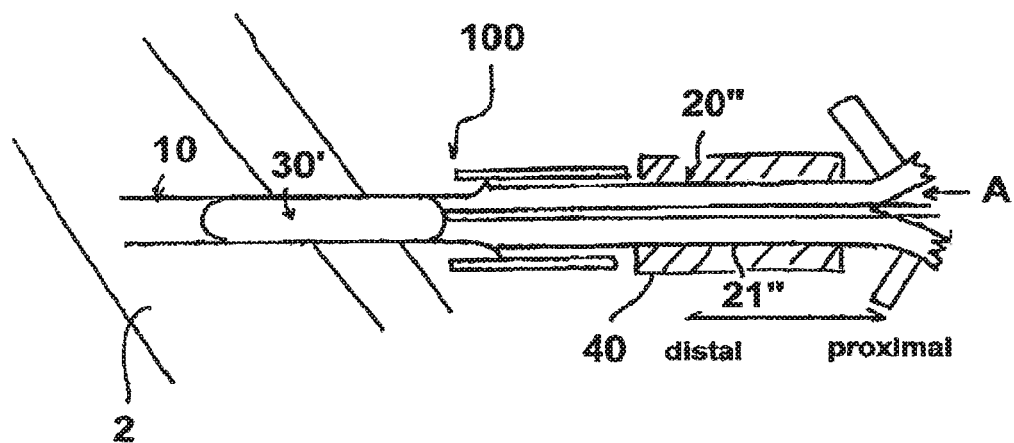

FIG. 9 shows the subsequent step, in which the distal pump unit 31' is located entirely in the lumen L1 of the first sheath 10. The fact that the distal pump unit 31' is located entirely in the lumen L1 of the first sheath 10 can be indicated, for example, by using a colored marking 50 which is applied to the outside of the shaft catheter 32'.

The second sheath 20", which is designed as a "peel-away" sheath, is then removed from the shaft catheter 32' by tearing open the peel-away sheath from the proximal end to the distal end and pulling it off the shaft catheter 32'. The directed tearing open from the proximal end to the distal end can be supported by notches A, however it is primarily based on the orientation of the molecule chains of the plastic material that is used from the proximal direction in the distal direction.

After the peel-away sheath has been removed, the pump 30' is guided further inside the lumen L1 of the first sheath 10 to the desired location.

The first sheath can optionally be advanced to the immediate vicinity of the site of use before or after the pump has been inserted using the distal sheath mouth. The first sheath has the required length to do so.

A reinforcement of the second sheath 20" is not required, in particular when pulling the distal pump unit 31' into the distal end of the second sheath lumen L2, because the risk of the shaft kinking during a pulling motion is significantly reduced.

When the pump is transferred from the second sheath to the first sheath, as shown based on FIGS. 7 to 9, the second sheath may comprise a reinforcing structure in form of an introduced wire, or the tubular section 21" of the sheath 20" is not produced from a flexible plastic material, but from a non-deformable plastic material or metal.

Another option for stabilizing the pump and the second sheath is that of holding the second sheath 20" by way of a supporting element 40 in form of a stable outer sleeve when advancing the pump 30' in the distal direction, which is to say in particular when transferring the pump 30' from the second sheath into the first sheath.

Hereafter, another possible variant of a method for inserting a pump into a left ventricle shall be described. As a preparatory measure, the pump is first filled with a sterile physiological salt solution and is thus completely freed from air. Then, the peel-away sheath located proximal of the distal pump unit is advanced to a potentially present outflow hose. The diameter of the peel-away sheath is 10 Fr, for example. After the peel-away sheath has been advanced to the outflow hose, the peel-away hose is surrounded by a sleeve-shaped element so as to hold the second sheath. The distal pump unit is then pulled into the peel-away sheath, optionally by performing a slight rotational movement, by performing a pulling motion in the proximal direction on the shaft catheter. The pump is advanced into the second sheath so far that a potentially present pigtail is likewise secured in the peel-away sheath. These steps make it possible to examine the functional capability of the pump even before surgery and to insert the pump only then into a sheath, without having to act under time pressure. For example, it is only then that the vascular system is punctured so as to insert the first sheath. However, so as to save time, it is thus also possible for an assistant to prepare the pump, while the user already carries out the puncturing.

After a 9 Fr introducer sheath, for example, has been introduced into the left ventricle, a potentially present dilator is pulled out of the introducer sheath and removed therefrom.

The pump, which is held in the peel-away sheath and which initially is, for example, enveloped by the sleeve so as to hold the second sheath, is then pushed into the sheath housing until the tip of the peel-away sheath strikes against a mechanical stop. The pump is then transferred from the peel-away sheath into the tubular section by pushing the shaft catheter. As soon as the distal pump unit has been completely transferred into the introducer sheath, as can be verified based on an optical marking on the catheter shaft, for example, the peel-away sheath can be torn open and pulled off the shaft catheter. The pump is then advanced inside the first sheath into the left ventricle. The first sheath is subsequently pulled back out of the left ventricle, to the point where the descending aorta begins.

The positioning of the distal pump unit in the left ventricle can be controlled by way of radioscopy, for example. For this purpose, an X-ray visible marking is located on the pump housing or in the vicinity thereof, for example on the catheter, or the pump housing itself is visible to X-rays. The discharge region of the pump, which is to say the discharge openings of an outflow hose, should likewise be located in the region of the ascending aorta. This can also be checked using an X-ray visible marking. A potentially present pigtail catheter tip should make contact with the tip of the left ventricle.

So as to remove the pump from the ventricle, the pump is retracted into the introducer sheath by means of a pulling force that is applied to the shaft catheter and is removed from the arterial vascular system in the compressed state. If the first sheath has already been shortened, the pump can also first be retracted a certain distance into the shaft catheter so as to compress the pump. For this purpose, the shaft catheter may comprise a pull-in funnel into which the pump can be pulled by pulling on the drive shaft. The first sheath and further remaining components are then removed from the vascular system.

The invention provides a particular advantage when a long sheath is used during the implantation and explanation of the pump. The long sheath is not only used, as is customary in the prior art, to insert the pump into an endogenous lumen, but also to guide the pump through the sheath lumen into the vicinity of the site of action. To this end it is advantageous in the medical field if the sheath has a length between 40 and 120 cm. The length is determined by the later site of action of the pump and the patient's physique.

If the pump is pulled out of the endogenous lumen together with the long sheath, bleeding of the femoral artery is stopped by means of a pressure dressing. As an alternative, the pump can be pulled out of the sheath lumen of the long sheath. A further guide wire can then be placed through the lumen of the sheath, and an element for closing the puncture can be guided via this guide wire after the sheath has been removed. This allows improved stemming of the bleeding to be achieved.

FIGS. 10 to 13 show in particular an embodiment of the first sheath according to the invention, comprising one or more clamping elements for fixing a tubular section 41 in a sheath housing 43.

Figure 10:
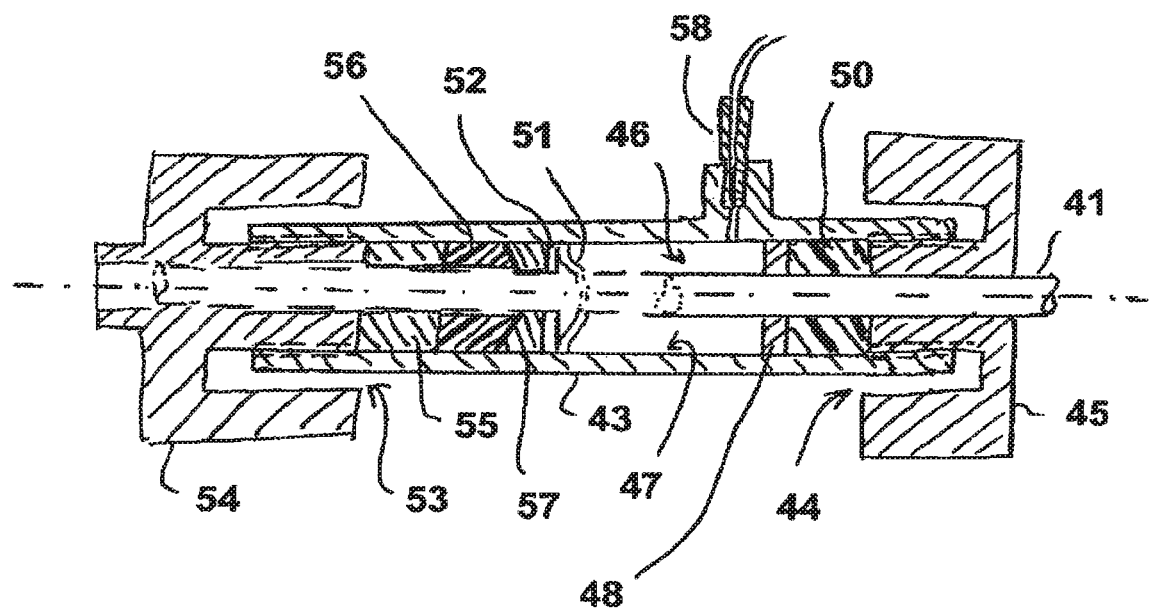
FIG. 10 is a longitudinal section through a sheath housing comprising a tubular section.

FIG. 10 shows a longitudinal section of a sheath housing 43, which substantially has the shape of a cylindrical sleeve which is closed at least at the distal end 44 facing the patient's body by a pressure screw 45. The sheath housing 43 has a continuous receiving channel 46 for a tubular section 41 of the first sheath. In the illustration of FIG. 10, coming from the patient's body, the tubular section 41 is shown continuously up to the flushing space 47 of the receiving channel 46, and then in dotted form in the proximal direction. This indicates that the tubular section 41 can be axially displaced relative to the sheath housing 43 inside the receiving channel 46 or, in other words, the sheath housing 43 can be displaced on the tubular section 41.

So as to insert a functional element, for example a pump, into the first sheath, the tubular section 41 is usually pulled out of the sheath housing 43 in the distal direction so far, or it is positioned during production of the first sheath, so that it ends approximately at the level of the first stop piece 48. A second sheath comprising a retracted pump, as described above, can be advanced up to this point, so as to then move the pump from the second sheath into the first sheath.

The first clamping element comprises elements such as the first pressure screw 45, a first clamping ring 50 made of an elastomeric material, and the first stop piece 48.

The pressure screw is screwed to the sheath housing by means of an external thread in an overlapping region with the distal end 44 of the sheath housing 43. Manually rotating the pressure screw 45 thus brings about a movement of the pressure screw in the axial direction, which results in axial compression or expansion of the clamping ring 50. During an axial compression, the clamping ring 50 tends to give way radially inward and outward so as to maintain the volume thereof and thus clamps the tubular section 41, because it experiences resistance at the proximal side by the first stop piece 48.

The tubular section 41 is thus axially fixed relative to the sheath housing 43. This fixation can easily be released by loosening the pressure screw 45, so that the tubular section 41 is then easy to axially displace in the sheath housing 43. To this end, when it is relaxed, the clamping ring can have an inside diameter that equal to or larger than the diameter of the first sheath.

So if the tubular section 41 is first pushed as far as possible into the patient's body to allow insertion of the pump, protected by the sheath, to the site of use, for example a ventricle, the tubular section 41 is pulled out after the pump has been removed and the sheath as a whole protrudes relatively little from the patient's body. The clamping element 48, 45, 50 can then be released and the sheath housing 43 can be pushed closer to the patient's body on the tubular section 41. The tubular section 41 then extends completely through the sheath housing 43 and optionally protrudes from the same in the proximal direction. Using means which will be described in more detail hereafter, the tubular section 41 can then be severed in some regions so as to remove the excess length.

A so-called combined haemostatic valve, which is composed of a dome valve 51 and a valve plate 52, is provided inside the sheath housing 43 to provide better sealing action. The valve plate closes the sheath housing 43 if at this point neither the tubular section 41 nor a shaft catheter extends through the receiving channel 46, while the dome valve 51 is optimized so as to provide tight sealing around a strand-shaped body, for example the tubular section or a catheter.

A further pressure screw 54 is provided at the proximal end 53 of the sheath housing 43, the pressure screw basically functioning in the same manner as the first pressure screw 45 and effecting the compression of a second clamping ring 56 relative to a second mechanical stop 57 via a pressure piece 55. A special feature that should be mentioned here is that the distal end of the second clamping ring 56 has a conical shape, which favors a deformation radially inward when exerting an axial pressure by way of the pressure screw 54. The second stop 57 has a conical design in the opposite direction. However, it is also possible at this point to use a non-conical clamping ring 56, and instead one which has a rectangular or round cross-section.

It is then possible to additionally dispose one or more further valves in the flushing space between the clamping element 48, 45, 50 and the flushing inlet 58, whereby it is assured that a fluid-tight connection exists between the tubular section 41 and the sheath housing 43, even if the clamping element 48, 45, 50 is released.

FIG. 10 schematically indicates a flushing element 58, which allows the flushing space 47 to be flushed with a liquid that prevents microbes from penetrating into the patient's body through the first sheath. This flushing is particularly effective if the tubular section 41 ends in the flushing space 47 or on the distal side thereof, so that the flushing liquid can reach both the outside and the inside of the tubular section 41.

Figure 11:
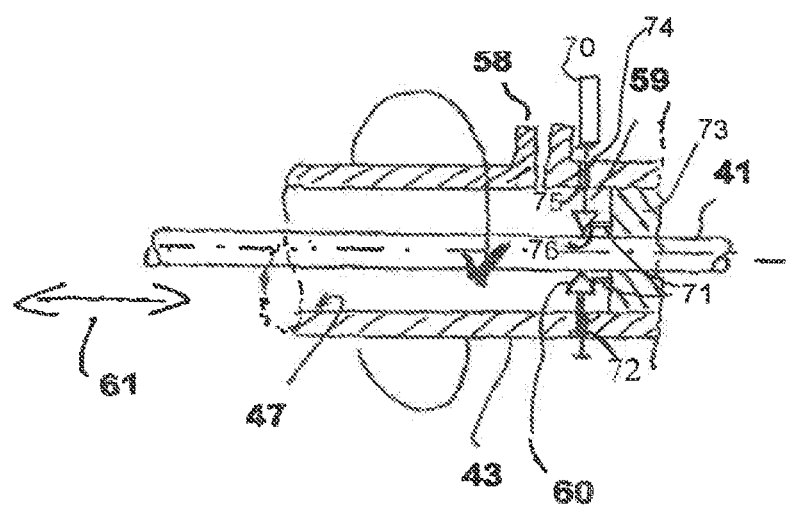
FIG. 11 is a longitudinal section through a portion of a sheath housing comprising a cutting element.

FIG. 11 shows, by way of example, the arrangement and operating principle of a cutting element according to the invention.

If no precut predetermined breaking points, or no predetermined breaking points that are predefined in another manner, for example by a predetermined molecule structure or regional weakening of the wall thickness of the tubular section 21, are provided, these can be introduced in a suitable manner when using the first sheath by way of a cutting element. In the region of the flushing space 47 of the sheath housing 43 in FIG. 11, a cutting element comprising blades 59, 60 is provided, which cuts the tubular section in the circumferential section, for example during a rotation of the sheath housing relative to the tubular section. It is also possible to introduce cuts in the axial direction.

For this purpose, the blades 59, 60 can also be disposed such that they cut in the longitudinal direction during a movement of the tubular section 41 in the axial direction, as indicated by the arrow 61. It is possible to provide blades both for cutting in the circumferential direction and for cutting in the longitudinal direction.

FIG. 11 also shows that the blades 59, 60 can be moved radially toward the tubular section 41 by actuation from outside the sheath housing 43. There, a guide 72 extending in the radial direction for one or more blade holders 70, a corresponding seal 75 and a suspension 74 can be provided, so that microbes are prevented from penetrating via this displacement element for the blades and the blades, when not actuated, radially have a distance from the tubular section 41. After use of the first sheath, it is then possible to manually apply pressure to the blades and the portion of the tubular section 41 that is not required can be cut off. A stop 71, prevents the cutting depth from exceeding a critical dimension and causing damage to a catheter which may be present inside the sheath.

The blades shown can also form a cutting element for a second sheath.

Figure 12:
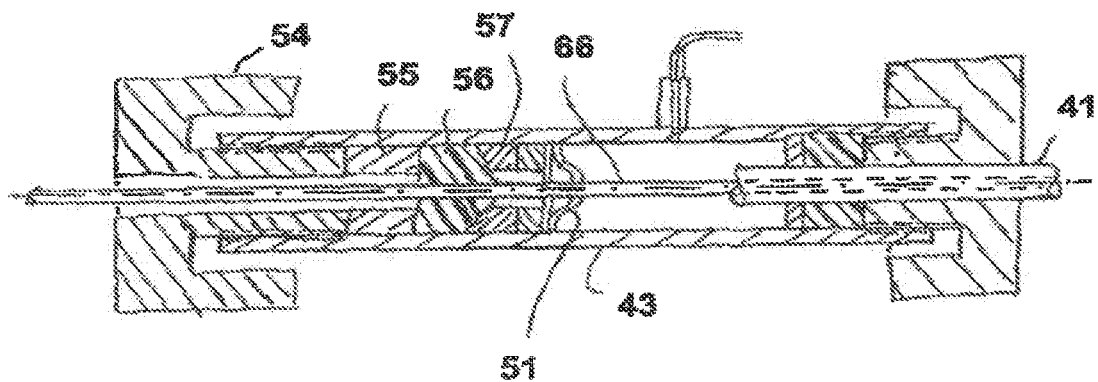
FIG. 12 is a longitudinal section through a sheath housing comprising a clamping element for the tubular section and a further clamping element.

FIG. 12 shows an advantageous use of the second clamping element on the proximal side of the sheath housing 43 after the tubular section 41 has been shortened, and a shaft catheter 61, leads out of the proximal end of the tubular section 41 and then on to a coupling element, which is not shown, for a drivable shaft of a pump and out of the sheath housing 43. The shaft catheter is sealed in the aforementioned dome seal 51, and the clamping element, together with the elements of the second pressure screw 54 and of the second clamping ring 56, which is axially compressed by the pressure piece 55 relative to the second stop 57, gives way radially inward far enough for the shaft catheter 61, which has a substantially smaller outside diameter than the tubular section 41 or a second sheath, to be clamped and in particular to be additionally sealed. Both the tubular section 41 and the shaft catheter 61 protruding therefrom can thus be fixed in the sheath housing 43.

The second clamping element is likewise suitable for fixing the second sheath with the second clamping ring 56, when inserting a second sheath into the sheath housing 43, such that the second sheath is sufficiently fixed relative to the sheath housing 43, and notably relative to the tubular section 41, so as to allow the shaft catheter 61 to be pushed through.

The first and second clamping rings 50, 56 can be produced from an elastomer, for example a rubber or a silicone elastomer, and can thus be fully elastic, but be deformable without being able to compress the volume. At this point, using an elastic foamed material in which some of the volume can be compressed is also conceivable.

Figure 13:
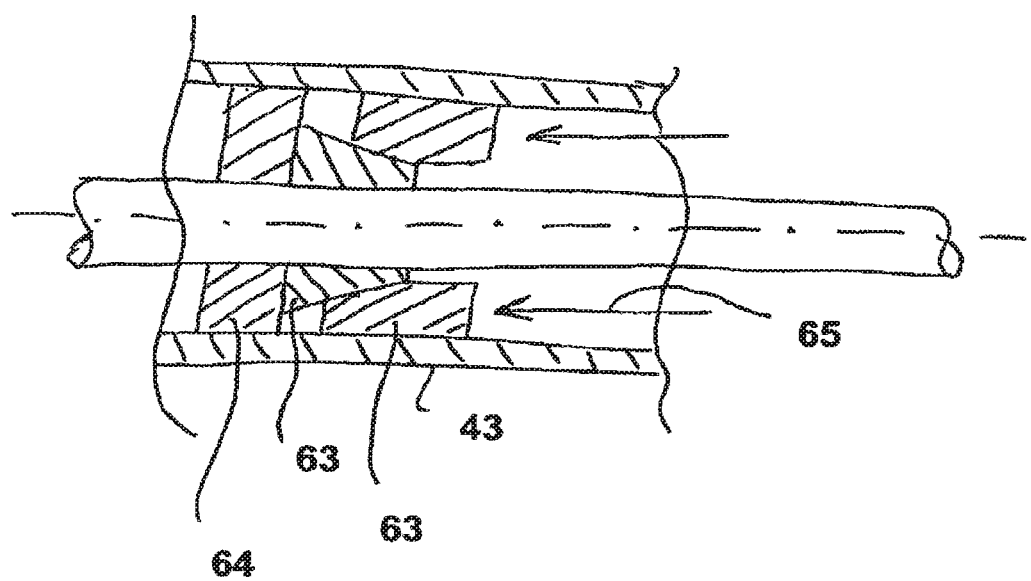
FIG. 13 is a longitudinal section through an alternative clamping ring comprising a conical pressure piece.

FIG. 13 is a schematic view of another type of a clamping ring 62, which can be produced from a plastic material or a metal, for example, and in particular can be slotted and thus be radially compressible. The slotted clamping ring 62 has a conical outside contour, against which the conical contour of a pressure piece 63 pushes so as to radially compress the clamping ring as soon as an axial pressure force is exerted on the pressure piece 63 in the direction of the arrow 65, for example by a pressure screw shown above. The slotted clamping ring 62 is axially fixed by the stop piece 64.

A first concept of the invention relates to a sheath device for inserting a catheter into a lumen, in particular of a patient's body, comprising a first sheath (10, 11, 13, 21, 21', 21", 41, 43) having a proximal end and a distal end, which is located in particular on the patient body side, wherein the first sheath comprises a sheath housing (13, 43) having a receiving channel, which hereafter is referred to as the first receiving channel, and a further receiving channel for receiving a tubular section, which extends distally from the sheath housing and which in particular runs coaxially relative to the first receiving channel and in which the tubular section can be axially displaced and fixed.

The first and the further receiving channels are located in particular coaxially relative to each other and axially behind each other, and the tubular section can also extend through both receiving channels.

A second concept of the invention relates to a sheath device according to the first concept, wherein the diameter of the first receiving channel differs from the diameter of the further receiving channel.

The diameter of the first receiving channel can be smaller or larger than the diameter of the further receiving channel. However, it is also conceivable for the diameter of the first receiving channel to substantially correspond to the diameter of the further receiving channel.

According to a third concept of the invention, a clamping element (54, 54', 55, 56, 56', 57, 57') for fixing a strand-shaped body in the first receiving channel and/or for fixing a tubular section (11, 21, 21', 21", 41) in the further receiving channel by way of clamping can be provided in the first receiving channel (46) and/or in the further receiving channel according to the first concept or the second concept of the invention.

At least one of the clamping elements (54, 54', 55, 56, 56', 57, 57') can, for example, be designed such that it selectively allows clamping of a strand-shaped body having a first diameter or of a strand-shaped body having a second diameter, wherein the first diameter is different from the second diameter.

For this purpose, for example, a clamping mechanism comprising a clamping screw can be provided, which has several preferred clamping positions. These can, for example, be implemented by various positions of the clamping screw.

According to a fourth concept of the invention, which relates to a sheath device according to the first, second or third concept, additionally a radial expansion of the first or further receiving channel containing a flushing element can be provided in the sheath housing (13, 43) in the region of the first receiving channel and/or the further receiving channel.

The flushing element can, for example, comprise one or more radial fluid connections for supplying and removing a fluid.

In the region of the radial expansion, for example at one of the axial ends thereof, additionally a valve can be provided for closing off the radial expansion in a fluid-tight manner.

The valve may comprise a valve plate and/or a dome valve.

A fifth concept of the invention relates to a sheath device according to the first or any one of the subsequent concepts (2 to 4) of the invention, wherein a cutting device comprising at least one blade is provided, which has at least one possible position, in which it radially protrudes into the first receiving channel or into the further receiving channel or into the expanded region, and more particularly into the flushing space.

For example, at least one blade that cuts in the circumferential direction of a receiving channel or a blade that cuts in the axial direction may be provided for this purpose. The respective blade(s) can each be displaceable in the radial direction with respect to the receiving channel or the expanded region between at least one cutting position and a non-cutting position, in particular a position that does not protrude into a receiving channel. The displacement can take place against the counterforce of a spring 76, which cooperates with the knife or a knife holder.

In addition, a fluid-tight guide channel can be provided for each of the knives.

A sixth concept of the invention relates to a sheath device according to the first or any one of the subsequent concepts (2 to 5) of the invention, comprising a tubular section that is located in the further receiving channel.

A seventh concept of the invention relates to a catheter device comprising a sheath device according to any one of the preceding concepts and comprising a catheter, which extends through the receiving channel on the inside and together with a second sleeve-shaped sheath, wherein the second sheath is fixed in the first receiving channel, in particular in a clamping element (54, 54', 55, 56, 56', 57, 57') of the first receiving channel.

An eighth concept of the invention relates to a method for inserting a catheter (32, 66) into a patient's body by means of a sheath device according to any one of the preceding concepts of the invention and by means of a second sheath (20, 20', 20'', 20'''), wherein first the second sheath, together with the catheter, is inserted into the first sheath (10, 11, 13, 21, 21', 21'', 41', 43), and more particularly up to the end of the tubular section and abutting the same, the second sheath is then fixed by means of a clamping element (54, 54', 55, 56, 56', 57, 57'), and thereafter the catheter is transferred from the second sheath into the first sheath.

A ninth concept of the invention relates to a method according to the ninth concept, wherein the second sheath (20, 20', 20'', 20''') is removed, in particular by tearing it open or off, after the catheter has been inserted into the first sheath.

A tenth concept of the invention relates to a method according to the eighth or ninth concept, wherein the catheter is fixed in a clamping element (54, 54', 55, 56, 56', 57, 57') after the second sheath (20, 20', 20'', 20''') has been removed.

An eleventh concept of the invention relates to a method for inserting a catheter into a patient's body by means of a sheath device according to any one of the preceding concepts of the invention, wherein a tubular section (11, 21, 21', 21'', 41) is introduced into the sheath housing (13, 43) and likewise is introduced into a lumen of a patient's body, wherein then a functional element is introduced into the lumen of the patient's body through the sheath device, wherein then the tubular section is pulled at least a certain distance out of the lumen of the patient's body, wherein the sheath housing is displaced in the distal direction relative to the tubular section, and wherein then the tubular section is fixed on the sheath housing by means of a clamping element and/or is cut off inside the sheath housing.

The invention claimed is:

1. An introducer sheath device comprising:
    a sheath housing having a guide channel extending in a radial direction;
    a first sheath located within the sheath housing and configured to move in a longitudinal direction relative to the sheath housing, the sheath configured to allow passage of a catheter therein; and
    a cutting device comprising
    a first blade moveably positioned between the sheath and the sheath housing,
    wherein the first blade is configured to cut the sheath as the first blade moves in the longitudinal direction relative to the sheath housing and wherein the guide channel is a fluid tight channel through the sheath housing.

2. The sheath device of claim 1, wherein the cutting device further comprises a second blade positioned opposite the first blade within the sheath housing.

3. The sheath device of claim 2, wherein the first blade and the second blade cut the sheath in the longitudinal direction during a movement of the first sheath in an axial direction.

4. The sheath device of claim 3, wherein the first blade cuts in the longitudinal direction, the second blade cuts in a circumferential direction, and wherein the cutting device further comprises a third blade, wherein the third blade cuts in the circumferential direction.

5. The sheath device of claim 1, wherein the guide channel extending in a radial direction comprises at least one of:
    at least one blade holder;
    a sealing element providing a fluid-tight connection between the sheath housing and the first sheath; or
    a suspension element.

6. The sheath device of claim 5, wherein the guide is configured to displace the first blade in the radial direction.

7. The sheath device of claim 6, wherein the first blade is displaceable between at least one cutting position and a non-cutting position.

8. The sheath device of claim 7, wherein in the non-cutting position the first blade does not protrude into a receiving channel of the first sheath.

9. The sheath device of claim 7, wherein the guide further comprises a spring which provides a counterforce for displacement of the first blade.

10. The sheath device of claim 1, wherein the fluid-tight guide channel encloses the first blade.

11. The sheath device of claim 1, further comprising a second sheath fixed within the first sheath, the second sheath configured to allow passage of the catheter therethrough.

12. The sheath device of claim 11, wherein the second sheath is fixed by a clamping element of the sheath housing.

13. The sheath device of claim 11, wherein the first sheath is configured to allow passage of the catheter from the second sheath into the first sheath.

14. The sheath device of claim 13, wherein the first blade is configured to cut the second sheath after passage of the catheter therethrough.

15. The sheath device of claim 1, wherein a blood pump is connected to a distal end of the catheter.

16. A method for using a sheath cutter device, the method comprising:
    inserting a first sheath into a sheath housing, the sheath housing including a first blade positioned between the sheath and the sheath housing;
    actuating a movement of the first blade in a radial direction within the sheath housing from a non-cutting position to a cutting position, wherein the movement of first blade is configured to cut the first sheath; and
    cutting the first sheath with the first blade.

17. The method of claim 16, wherein the first blade is actuated by a guide having at least one of a blade holder, a sealing element, or a suspension element.

18. The method of claim 16, further comprising:
    clamping a second sheath within the first sheath, wherein the second sheath is
    clamped by a clamping element of the sheath housing.

19. The method of claim 18, wherein the second sheath encloses a catheter, and wherein the first sheath and the second sheath are configured to allow passage of the catheter therethrough.

20. The method of claim 19, further comprising:
    transferring the catheter from the second sheath to the first sheath.

21. The method of claim 20, further comprising:
    actuating the movement of the first blade within the sheath housing, wherein the movement of the first blade is configured to cut the second sheath; and
    cutting the second sheath with the first blade.

22. The sheath device of claim 2, wherein the first blade cuts in the longitudinal direction, and the second blade cuts in a circumferential direction.

* * * * *